United States Patent [19]

Hansen et al.

[11] Patent Number: 4,472,305

[45] Date of Patent: Sep. 18, 1984

[54] HEXAPEPTIDE AMIDES

[75] Inventors: Philip E. Hansen, Schodack; Barry A. Morgan, Colonie, both of N.Y.

[73] Assignee: Sterling Drug Inc., New York, N.Y.

[21] Appl. No.: 495,383

[22] Filed: May 17, 1983

[51] Int. Cl.³ .......................................... C07C 103/52
[52] U.S. Cl. ............................................ 260/112.5 R
[58] Field of Search ................................ 260/112.5 R

[56] References Cited

U.S. PATENT DOCUMENTS 4,161,522 7/1979 Hamburger .................. 260/112.5 R

OTHER PUBLICATIONS

Sandberg et al., J. Med. Chem., vol. 25, No. 9, pp. 1009–1015, 1982.

Chorev et al., Peptides 1980, Proceedings of the Sixteenth European Peptide Symposium, Helsinger, Denmark, Aug. 31–Sep. 6, 1980, edited by K. Bunfeldt, Scriptor, Copenhagen, 1981, paper entitled "Spatial Requirements at the N-Acylating Residue of Substance P Partial Sequence", pp. 451–456.

*Primary Examiner*—Delbert R. Phillips
*Attorney, Agent, or Firm*—Theodore C. Miller; Paul E. Dupont; B. Woodrow Wyatt

[57] ABSTRACT

N-Terminal L-prolyl or D-prolyl hexapeptide amides useful as Substance P agonists and/or antagonists and as analgesics and/or antihypertensives and a process for preparing them are disclosed.

10 Claims, No Drawings

HEXAPEPTIDE AMIDES

BACKGROUND OF THE INVENTION

1. Field of the Invention

The invention relates to hexapeptide amides which are useful as Substance P agonists and/or antagonists and are therefore useful as analgesics and/or as antihypertensives.

2. Information Disclosure Statement

Substance P (SP) is an endogenous undecapeptide amide and a putative neurotransmitter of mammalian central nervous systems (Sandberg et al., J. Med. Chem., vol. 25, no. 9, pp. 1009-1015, 1982) having the following structural formula, wherein the amino acid units are numbered from 1 through 11 beginning with the N-terminal amino acid:

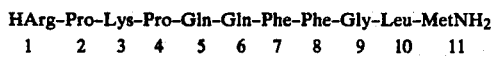

The hexapeptide amide having the structural formula

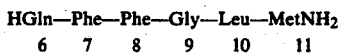

is referred to as SP$_{6-11}$.

Chorev et al. (Peptides 1980, Proceedings of the Sixteenth European Peptide Symposium, Helsinger, Denmark, August 31–September 6, 1980 Edited by K. Bunfeldt, Scriptor, Copenhagen, 1981, paper entitled "Spatial Requirements at the N-Acylating Residue of Substance P Partial Sequence", pp. 451–456) describes as SP Analog No. 13 in Table 1 at page 455 [Pro$^6$]SP$_{6-11}$, which is SP$_{6-11}$ wherein L-glutaminyl at position 6 is replaced by L-prolyl.

SUMMARY OF THE INVENTION

In a first composition of matter aspect the invention is the hexapeptide amide having the structural formula Formula I

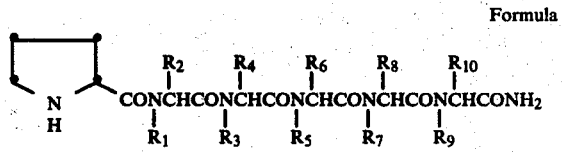

wherein:

$R_1$, $R_5$, $R_7$ and $R_9$ taken alone are each independently hydrogen or methyl;

$R_2$ is phenyl, benzyl, p-chlorobenzyl, 4-pyridylmethyl or 3-indolylmethyl;

$R_3$ is hydrogen, methyl, benzyl, or 2-phenylethyl;

$R_4$ is hydrogen, benzyl, p-chlorobenzyl, 2-phenylethyl or 4-pyridylmethyl;

$R_6$ taken alone is hydrogen, methyl, benzyl, 4-pyridylmethyl, 3-indolylmethyl, aminomethyl, 4-aminobutyl, 3-guanidinopropyl or 2-carboxyethyl;

$R_6$ taken together with $R_7$ is ethylene;

$R_8$ is 2-methylpropyl or dimethylaminomethyl; and $R_{10}$ is butyl or 2-methylthioethyl; and wherein each of the six amino acid moieties has the R or S configuration except the amino acid moiety bearing $R_2$ when $R_2$ is benzyl, which can only have the R configuration; or a pharmaceutically acceptable acid addition salt thereof.

In a second composition of matter aspect the invention is the hexapeptide amide having the structural formula

    Formula II wherein $X_2$ is DPhe or MePhe or a pharmaceutically acceptable acid addition salt thereof.

In a third composition of matter aspect the invention is the hexapeptide amide having the structural formula

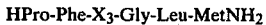    Formula III wherein $X_3$ is DPhe, MePhe, D, LBpa, DBpa or LBpa or a pharmaceutically acceptable acid addition salt thereof.

In a fourth composition of matter aspect the invention is the hexapeptide amide having the structural formula HPro-Phe-Phe-X$_4$-Leu-MetNH$_2$    Formula IV wherein $X_4$ is DAla, Sar, LDap, Glu, LBpa or DBpa or a pharmaceutically acceptable acid addition salt thereof.

In a fifth composition of matter aspect the invention is the hexapeptide amide having the structural formula

    Formula V wherein $X_5$ is DLeu, MeLeu or Gal or a pharmaceutically acceptable acid addition salt thereof.

In a sixth composition of matter aspect the invention is the hexapeptide amide having the structural formula

    Formula VI wherein $X_6$ is DMet or Nle or a pharmaceutically acceptable acid addition salt thereof.

In a seventh composition of matter aspect the invention is the hexapeptide having the structural formula

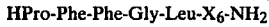    Formula VII or a pharmaceutically acceptable acid solution salt thereof.

In an eighth composition of matter aspect the invention is the hexapeptide having the structural formula

    Formula VIII or a pharmaceutically acceptable acid addition salt thereof.

The hexapeptide amides of Formulas I–VIII are useful as Substance P agonists and/or antagonists and are therefore useful as analgesics and/or as antihypertensives.

In a process aspect the invention is the process of preparing a hexapeptide amide of Formulas I–VIII which comprises condensing the corresponding amino acid and/or peptide moieties by a 1+5, 2+4, 3+3, 4+2 or 5+1 hexapeptide forming method, concomitantly protecting and deprotecting the N-terminal α-amino group, the C-terminal carboxyl group and any side chain amino or carboxyl group as required.

In all of the hexapeptide amides of Formulas I–VIII the N-terminal amino acid moiety is L-prolyl or D-prolyl. The amino acid moieties are considered as being numbered successively by the integers from 1 through 6 beginning on the left with L-prolyl or D-prolyl and ending on the right with the amino acid moiety bearing the terminal primary amide group. Thus, a 1+5 peptide condensation in accordance with the process aspect of the invention is a condensation of amino acid moiety 1 with pentapeptide moiety 2-6 with protection and deprotection as required. Similarly, a 2+4 peptide condensation is a condensation of dipeptide moiety 1-2 with tetrapeptide moiety 3-6; a 3+3 peptide condensation is a condensation of tripeptide moiety 1-3 with tripeptide moiety 4-6; a 4+2 peptide condensation is a condensation of tetrapeptide moiety 1-4 with dipeptide moiety 5-6; and a 5+1 peptide condensation is a condensation of pentapeptide moiety 1-5 with amino acid moiety 6.

In Formulas II-VIII above and in the examples below the symbols for the amino acid moieties, which do not include the N-terminal and C-terminal groups, have the following meanings:

| | |
|---|---|
| Pro: | L-prolyl |
| Phe: | L-phenylalanyl |
| Gly: | glycyl |
| Leu: | L-leucyl |
| Met: | L-methionyl |
| DPhe: | D-phenylalanyl |
| MePhe: | L-N—methylphenylalanyl |
| D,LBpa: | racemic β-(4-pyridyl)alanyl |
| DBpa: | D-β-(4-pyridyl)alanyl |
| LBpa: | L-β-(4-pyridyl)alanyl |
| DAla: | D-alanyl |
| Sar: | L-sarcosinyl |
| LDap: | L-2,3-diaminopropionyl (L-β-aminoalanyl) |
| DLeu: | D-leucyl |
| MeLeu: | L-N—methylleucyl |
| Gal: | L-β-dimethylaminoalanyl |
| DMet: | D-methionyl |
| Nle: | L-norleucyl |
| DPro: | D-prolyl |
| CabLeu: | $\begin{array}{c} CH_2-CH_2 \\ \mid \quad \mid \\ NHCHCONCHCO \\ \mid \\ CH_2CH(CH_3)_2 \end{array}$ (cyclo-L-2-aminobutyryl-L-leucyl) |
| DTrp: | D-tryptophyl |
| GLu: | L-glutamyl |
| DPhg: | D-phenylglycyl |
| Hfe: | L-homophenylalanyl |
| Bgl: | N—benzylglycyl |
| Pgl: | N—(2-phenylethyl)glycyl |
| DLys: | D-lysyl |
| DArg: | D-arginyl |
| MeMet: | L-N—methylmethionyl |
| Pcp: | L-p-chlorophenylalanyl |
| MeDTrp: | D-$N^2$—methyltryptophyl |
| MeNle: | L-N—methylnorleucyl |

DETAILED DESCRIPTION OF THE INVENTION INCLUSIVE OF THE PREFERRED EMBODIMENTS

PREPARATION OF THE COMPOUNDS

The protection, activation, condensation and deprotection steps required to prepare the compounds of Formulas I-VIII are carried out using the methods of peptide synthesis generally described by Houben Weyl "Methoden der Organischen Chemie" (vol. 16, parts I and II, "Synthese von Peptiden", Thieme, 1974) and Gross and Meienhofer "The Peptides" (vol. 1, "Major Methods of Peptide Bond Formation", Academic Press, 1979).

The suitably carboxyl-activated derivatives of the amino acid and peptide intermediates can be formed and used with or without being isolated and include the acyl halides and pseudohalides, especially the acyl azides; the anhydrides, especially the mixed anhydrides and most especially the mixed anhydride with diphenylphosphinyl chloride or isobutyl chloroformate; derivatives formed by addition reactions, especially using dicyclohexylcarbodiimide; displaceable acyl derivatives of heterocyclic nitrogen; ring-openable activated heterocyclic systems; acylphosphonium derivatives; activated esters, especially 1-hydroxybenzotriazole (HOBt), N-hydroxysuccinimide (HOSu) and pentafluorophenyl (PFP) esters; and polymeric (solid phase) derivatives.

It is necessary that the N-terminal α-amino group be protected during the peptide forming steps. The preferred α-amino protecting groups are benzyloxycarbonyl (Z), which can be removed by catalytic hydrogenation using palladium as catalyst or by hydrogen bromide in acetic acid, and t-butoxycarbonyl (Boc), which can be removed by acidic cleavage, for example, with hydrogen chloride in a suitable solvent or trifluoroacetic acid with or without a solvent. A protecting group which can be removed in the presence of benzyloxycarbonyl or t-butoxycarbonyl under basic conditions, for example piperidine in dimethylformamide, is 9-fluorenylmethoxycarbonyl (Fmoc). Amino groups in the side chains of basic amino acids can be protected by benzyloxycarbonyl, t-butoxycarbonyl or p-toluenesulfonyl (Tos), the last of which can be removed with liquid hydrogen fluoride containing anisole as a cation scavenger.

The C-terminal carboxyl group must also be protected during the peptide forming steps. That of the compounds of Formulas I-VIII is protected as the amide, which is a required structural feature thereof and is therefore not removed. The C-terminal carboxyl groups and any side chain carboxyl group of the intermediate amino acids and peptides can be protected as the carboxylate salt, the t-butyl (tBu) ester, which can be removed by acidic cleavage, for example, with hydrogen chloride in a suitable solvent or trifluoroacetic acid, or the benzyl (Bz) ester, which can be removed by catalytic hydrogenation using palladium as catalyst.

The intermediate amino acids and peptides and other synthetic intermediates necessary to prepare the compounds of Formulas I-VIII are known classes of compounds and are commercially available or can be made by methods specifically or generally described in the chemical literature.

The acid addition salts of the compounds of Formulas I-VIII are prepared by conventional methods from any of the pharmaceutically acceptable organic and inorganic acids. Of the inorganic acids hydrochloric acid and phosphoric acid are particularly preferred. Of the organic acids acetic acid is particularly preferred.

The compounds of Formulas I-VIII and the acid addition salts thereof are hydrophilic and may form solvates with water or hydrophilic organic solvents or mixtures thereof. If the resulting products are crystalline, they are purified by recrystallization. If they are non-crystalline, which is generally so, they are purified by high pressure liquid chromatography or column chromatography and/or isolated by lyophilization.

In the preparations described below structures of products are inferred from known structures of starting materials and expected courses of preparative reactions. Structural confirmation and estimation of purity of starting materials and products are measured by melting temperature range (m.r.), optical rotation ($[\alpha]_D^{25}$), elemental analysis, infrared (IR) spectral analysis, ultraviolet (UV) spectral analysis, mass spectral (MS) analysis, nuclear magnetic resonance (NMR) spectral analysis, gas chromatography (GLC), column chromatography, high pressure liquid chromatography (HPLC), thin layer chromatography (TLC) and/or amino acid analysis.

EXAMPLE 1

HPro-Phe-Phe-DAla-Leu-MetNH$_2$

Condensation of ZPheOH (11.7 g.) and HPheOMe (9.0 g.) by the mixed anhydride method using isobutyl chloroformate gave ZPhe-PheOMe in 82% yield. Debenzyloxycarbonylation of ZPhe-PheOMe (13.0 g.) by hydrogenation with palladium catalyst gave HPhe-PheOMe in 86% yield. Condensation of BocProOH (5.04 g.) and HPhe-PheOMe (8.5 g.) by the mixed anhydride method using isobutyl chloroformate gave BocPro-Phe-PheOMe in 63% yield. Hydrazinolysis of BocPro-Phe-PheOMe (4.5 g.) gave BocPro-Phe-PheNHNH$_2$ in 93% yield.

Condensation of BocLeuOH (5.57 g.) and HMetNH$_2$ (4.13 g.) by the mixed anhydride method using isobutyl chloroformate gave BocLeu-MetNH$_2$ in 77% yield. De-t-butoxycarbonylation of BocLeu-MetNH$_2$ (6.0 g.) using hydrogen chloride in ethyl acetate gave HLeu-MetNH$_2$ hydrochloride salt in 75% yield. Condensation of BocDAlaOPFP (1.74 g.) and HLeu-MetNH$_2$ gave (1.49 g.) by the activated ester method gave BocDAla-Leu-MetNH$_2$ in 70% yield. De-t-butoxycarbonylation of BocDAla-Leu-MetNH$_2$ (1.53 g.) using hydrogen chloride in dioxane gave HDALa-Leu-MetNH$_2$ in 65% yield.

Condensation of BocPro-Phe-PheNHNH$_2$ (1.31 g.) and HDAla-Leu-MetNH$_2$ (0.85 g.) by the acyl azide method (Yajima et al., Chem. Pharm. Bull., vol. 19, p. 1900, 1971) gave BocPro-Phe-Phe-DAla-Leu-MetNH$_2$ in 66% yield. De-t-butoxycarbonylation of BocPro-Phe-Phe-DAla-Leu-MetNH$_2$ (1.10 g.) using hydrogen chloride in acetic acid gave HPro-Phe-Phe-DAla-Leu-MetNH$_2$, which was isolated as the amorphous white solid phosphate (1:1) salt sesquihydrate in 66% yield.

EXAMPLE 2

HPro-Phe-MePhe-Gly-Leu-MetNH$_2$

Condensation of BocProOSu (2.2 g.) and HPheOH (1.74 g.) by the salt coupling method gave BocPro-PheOH in 86% yield.

Condensation of BocMePheOH (5.0 g.) and HGlyOBz (3.75 g.) by the mixed anhydride method using isobutyl chloroformate gave BocMePhe-GlyOBz in 52% yield. De-t-butoxycarbonylation of BocMePhe-GlyOBz (2.0 g.) using hydrogen chloride in ethyl acetate gave HMePhe-GlyOBz in 95% yield.

Condensation of BocPro-PheOH (1.48 g.) and HMePhe-GlyOBz (1.48 g.) using dicyclohexylcarbodiimide and N-hydroxysuccinimide gave BocPro-Phe-MePhe-GlyOBz in 55% yield. Debenzylation of BocPro-Phe-MePhe-GlyOBz (0.95 g.) by hydrogenation with palladium catalyst gave BocPro-Phe-MePhe-GlyOH in 100% yield.

Condensation of BocPro-Phe-MePhe-GlyOH (0.76 g.) and HLeu-MetNH$_2$ hydrochloride salt (Example 1, 0.39 g.) using dicyclohexylcarbodiimide and N-hydroxysuccinimide gave BocPro-Phe-MePhe-Gly-Leu-MetNH$_2$ in 100% yield. De-t-butoxycarbonylation of BocPro-Phe-MePhe-Gly-Leu-MetNH$_2$ (1.07 g.) using hydrogen chloride in acetic acid gave HPro-Phe-MePhe-Gly-Leu-MetNH$_2$, which was isolated as the amorphous white solid phosphate (1:1) salt dihydrate in 22% yield.

EXAMPLE 3

HPro-Phe-Phe-Sar-Leu-MetNH$_2$

Condensation of BocSarOPFP (3.43 g.) and HLeu-MetNH$_2$ (Example 1, 2.98 g.) by the activated ester method gave BocSar-Leu-MetNH$_2$ in 75% yield. De-t-butoxycarbonylation of BocSar-Leu-MetNH$_2$ (3.04 g.) using hydrogen chloride in acetic acid gave HSar-Leu-MetNH$_2$ in 100% yield.

Condensation of BocPro-Phe-PheNHNH$_2$ (Example 1, 1.35 g.) and HSar-Leu-MetNH$_2$ (0.95 g.) by the acyl azide method (Yajima et al., Chem. Pharm. Bull., vol. 19, p. 1900, 1971) gave BocPro-Phe-Phe-Sar-Leu-MetNH$_2$ in 45% yield. De-t-butoxycarbonylation of BocPro-Phe-Phe-Sar-Leu-MetNH$_2$ (0.90 g.) using hydrogen chloride in acetic acid gave HPro-Phe-Phe-Sar-Leu-MetNH$_2$, which was isolated as the amorphous white solid phosphate (1:1) salt sesquihydrate in 59% yield.

EXAMPLE 4

HPro-Phe-Phe-Gly-DLeu-MetNH$_2$

Condensation of BocDLeuOH (2.49 g.) and HMetNH$_2$ (1.85 g.) by the mixed anhydride method using isobutyl chloroformate gave BocDLeu-MetNH$_2$ in 47% yield. De-t-butoxycarbonylation of BocDLeu-MetNH$_2$ (1.70 g.) using hydrogen chloride in acetic acid gave HDLeu-MetNH$_2$ in 78% yield. Condensation of BocGlyOSu (1.8 g.) and HDLeu-MetNH$_2$ (1.0 g.) by the activated ester method gave BocGly-DLeu-MetNH$_2$ in 95% yield. De-t-butoxycarbonylation of BocGly-DLeu-MetNH$_2$ (1.35 g.) using hydrogen chloride in acetic acid gave HGly-DLeu-MetNH$_2$ in 55% yield.

Condensation of BocPro-Phe-PheNHNH$_2$ (Example 1, 0.93 g.) and HGly-DLeu-MetNH$_2$ (0.63 g.) by the acyl azide method (Yajima et al., Chem. Pharm. Bull., vol. 19, p. 1900, 1971) gave BocPro-Phe-Phe-Gly-DLeu-MetNH$_2$ in 59% yield. De-t-butoxycarbonylation of BocPro-Phe-Phe-Gly-DLeu-MetNH$_2$ (0.88 g.) using hydrogen chloride in acetic acid gave HPro-Phe-Phe-Gly-DLeu-MetNH$_2$, which was isolated as the amorphous white solid phosphate (1:1) salt in 59% yield.

EXAMPLE 5

HPro-Phe-Phe-Gly-MeLeu-MetNH$_2$

Condensation of BocPheOH (13.3 g.) and HGlyOBz p-toluenesulfonate salt (17.9 g.) by the mixed anhydride method using isobutyl chloroformate gave BocPhe-GlyOBz in 71% yield. De-t-butoxycarbonylation of BocPhe-GlyOBz (9.1 g.) using methanesulfonic acid in tetrahydrofuran gave HPhe-GlyOBz methane-sulfonate salt in 70% yield. Condensation of BocPro-PheOH (Example 2, 4.3 g.) and HPhe-GlyOBz methansulfonate salt (4.9 g.) using dicyclohexylcarbodiimide and N-hydroxysuccinimide gave BocPro-Phe-Phe-GlyOBz in 76% yield. Debenzylation of BocPro-Phe-Phe-GlyOBz (4.0 g.) by hydrogenation with palladium catalyst gave BocPro-Phe-Phe-GlyOH in 90% yield.

Methylation of BocLeuOH (12.5 g.) using sodium hydride and methyl iodide gave BocMeLeuOH in 73% yield. Condensation of BocMeLeuOH (3.7 g.) and HMetNH$_2$ hydrochloride salt (2.8 g.) by the mixed anhydride method using isobutyl chloroformate gave BocMeLeu-MetNH$_2$ in 56% yield. De-t-butoxycarbonylation of BocMeLeu-MetNH$_2$ (3.3 g.) using hydrogen chloride in ethyl acetate gave MeLeu-MetNH$_2$ in 64% yield.

Condensation of BocPro-Phe-Phe-GlyOH (2.8 g.) and MeLeu-MetNH$_2$ (1.6 g.) using dicyclohexylcarbodiimide and N-hydroxysuccinimide gave BocPro-Phe-Phe-Gly-MeLeu-MetNH$_2$ in 49% yield. De-t-butoxycarbonylation of BocPro-Phe-Phe-GlyMeLeu-MetNH$_2$ using hydrogen chloride in acetic acid gave HPro-Phe-Phe-Gly-MeLeu-MetNH$_2$, which was isolated as the amorphous white solid free base in 36% yield.

EXAMPLE 6

HPro-Phe-Phe-Gly-Leu-DMetNH$_2$

Condensation of BocLeuOH (3.49 g.) and HDMetNH$_2$ (2.0 g.) by the mixed anhydride method using isobutyl chloroformate gave BocLeu-DMetNH$_2$ in 70% yield. De-t-butoxycarbonylation of BocLeu-DMetNH$_2$ (2.74 g.) using hydrogen chloride in ethyl acetate gave HLeu-DMetNH$_2$ in 91% yield. Condensation of BocGlyOSu (2.66 g.) and HLeu-DMetNH$_2$ (1.95 g.) by the active ester method gave BocGly-Leu-DMetNH$_2$ in 92% yield. De-t-butoxycarbonylation of BocGly-Leu-DMetNH$_2$ (2.30 g.) using hydrogen chloride in acetic acid gave HGly-Leu-DMetNH$_2$ in 79% yield.

Condensation of BocPro-Phe-PheNHNH$_2$ (Example 1, 1.93 g.) and HGly-Leu-DMetNH$_2$ (1.31 g.) by the acyl azide method (Yajima et al., Chem. Pharm. Bull., vol. 19, p. 1900, 1971) gave BocPro-Phe-Phe-Gly-Leu-DMetNH$_2$ in 60% yield. De-t-butoxycarbonylation of BocPro-Phe-Phe-Gly-Leu-DMetNH$_2$ (1.6 g.) using hydrogen chloride in acetic acid gave HPro-Phe-Phe-Gly-Leu-DMetNH$_2$, which was isolated as the amorphous white solid phosphate (1:1) slat sesquihydrate in 72% yield.

EXAMPLE 7

HPro-Phe-DPhe-Gly-Leu-MetNH$_2$

Condensation of ZPheOH (7.5 g.) and HDPheOMe (5.4 g.) by the mixed anhydride method using isobutyl chloroformate gave ZPhe-DPheOMe in 66% yield. Debenzyloxycarbonylation of ZPhe-DPheOMe (6.9 g.) by hydrogenation with palladium catalyst gave HPhe-DPheOMe in 100% yield. Condensation of BocProOH (3.23 g.) and HPhe-DPheOMe (4.9 g.) by the mixed anhydride method using isobutyl chloroformate gave BocPro-Phe-DPheOMe in 70% yield. Hydrazinolysis of BocPro-Phe-DPheOMe (5.0 g.) gave BocPro-Phe-DPheNHNH$_2$ in 84% yield.

Condensation of BocGlyOH (4.4 g.) and HLeu-MetNH$_2$ hydrochloride salt (Example 1, 7.5 g.) using dicyclohexylcarbodiimide and N-hydroxysuccinimide gave BocGly-Leu-MetNH$_2$ in 51% yield. De-t-butoxycarbonylation of BocGly-Leu-MetNH$_2$ using hydrogen chloride in acetic acid gave HGly-Leu-MetNH$_2$ hydrochloride salt in 56% yield.

Condensation of BocPro-Phe-DPheNHNH$_2$ (2.44 g.) and HGly-Leu-MetNH$_2$ hydrochloride salt (1.6 g.) by the acyl azide method (Yajima et al., Chem. Pharm. Bull., vol. 19, p. 1900, 1971) gave BocPro-Phe-Phe-Gly-Leu-MetNH$_2$ in 79% yield. De-t-butoxycarbonylation of BocPro-Phe-Phe-Gly-Leu-MetNH$_2$ using hydrogen chloride in acetic acid gave HPro-Phe-Phe-Gly-Leu-MetNH$_2$, which was isolated as the amorphous white solid hydrochloride salt monohydrate in 31% yield.

EXAMPLE 8

HPro-Phe-Phe-Gly-Leu-NleNH$_2$

Condensation of BocLeuOH (2.0 g.) and HNleNH$_2$ (1.0 g.) by the mixed anhydride method using isobutyl chloroformate gave BocLeu-NleNH$_2$ in 75% yield. De-t-butoxycarbonylation of BocLeu-NleNH$_2$ (1.42 g.) using hydrogen chloride in dioxane gave HLeu-NleNH$_2$ in 88% yield. Condensation of ZGlyOSu (1.91 g.) and HLeu-NleNH$_2$ (0.95 g.) by the activated ester method gave ZGly-Leu-NleNH$_2$ in 79% yield. Debenzyloxycarbonylation of ZGly-Leu-NleNH$_2$ (1.40 g.) by hydrogenation with palladium catalyst gave HGly-Leu-NleNH$_2$ in 67% yield.

Condensation of BocPro-Phe-Phe-PheNHNH$_2$ (Example 1, 1.09 g.) and HGly-Leu-NleNH$_2$ (0.70 g.) by the acyl azide method (Yajima et al., Chem. Pharm. Bull., vol. 19, p. 1900, 1971) gave BocPro-Phe-Phe-Gly-Leu-NleNH$_2$ in 69% yield. De-t-butoxycarbonylation of BocPro-Phe-Phe-Gly-Leu-NleNH$_2$ (1.0 g.) using hydrogen chloride in acetic acid gave HPro-Phe-Phe-Gly-Leu-NleNH$_2$, which was isolated as the amorphous white solid phosphate (1:1) salt sesquihydrate in 65% yield.

EXAMPLE 9

HPro-DPhe-Phe-Gly-Leu-MetNH$_2$

Condesation of BocProOH (6.46 g.) and N-hydroxysuccinimide (3.5 g.) using dicyclohexylcarbodiimide gave BocProOSu in 75% yield. Condensation of BocProOSu (5.0 g.) and HDPheOH (2.75 g.) by the salt coupling method gave BocPro-DPheOH in 67% yield. Condensation of BocPro-DPheOH (3.98 g.) and HPheOMe hydrochloride salt (2.4 g.) using dicyclohexylcarbodiimide and N-hydroxysuccinimide gave BocPro-DPhe-PheOMe in 74% yield. Hydrazinolysis of Boc-Pro-DPhe-PheOMe (3.14 g.) gave BocPro-DPhe-PheNHNH$_2$ in 79% yield.

Condensation of BocPro-DPhe-PheNHNH$_2$ (1.98 g.) and HGly-Leu-MetNH$_2$ hydrochloride salt (Example 7, 1.3 g.) by the acyl azide method (Yajima et al., Chem. Pharm. Bull., vol. 19, p. 1900, 1971) gave BocPro-DPhe-Phe-Gly-Leu-MetNH$_2$ in 82% yield. De-t-butoxycarbonylation of BocPro-DPhe-Phe-Gly-Leu-MetNH$_2$ (1.8 g.) using hydrogen chloride in acetic acid gave HPro-DPhe-Phe-Gly-Leu-MetNH$_2$, which was isolated as the amorphous white solid phosphate (1:1) salt monohydrate in 59% yield.

EXAMPLE 10

HDPro-Phe-Phe-Gly-Leu-MetNH$_2$

Condensation of BocDProOH (1.51 g.) and HPhe-PheOMe (2.53 g.) by the mixed anhydride method using isobutyl chloroformate gave BocDPro-Phe-PheOMe in 75% yield. Hydrazinolysis of BocDPro-Phe-PheOMe (2.00 g.) gave BocDPro-Phe-PheNHNH$_2$ in 79% yield.

Condensation of BocDPro-Phe-PheNHNH$_2$ (0.932 g.) and HGly-Leu-MetNH$_2$ hydrochloride salt (Example 7, 0.630 g.) by the acyl azide method (Yajima et al., Chem. Pharm. Bull., vol. 19, p. 1900, 1971) gave BocDPro-Phe-Phe-Gly-Leu-MetNH$_2$ in 58% yield. De-t-butoxycarbonylation of BocDPro-Phe-Phe-Gly-Leu-MetNH$_2$ (0.838 g.) using hydrogen chloride in acetic acid gave HDPro-Phe-Phe-Gly-Leu-MetNH$_2$, which was isolated as the amorphous white solid phosphate (1:1) salt sesquihydrate in 72% yield.

EXAMPLE 11

HPro-Phe-MePhe-Sar-Leu-MetNH$_2$

Condensation of BocPheOPFP (8.63 g.) and MePHeOMe (5.50 g.) by the active ester method gave BocPhe-MePheOMe in 95% yield. De-t-butoxycarbonylation of BocPhe-MePheOMe using hydrogen chloride in ethyl acetate gave HPhe-MePHeOMe in 48% yield. Condensation of BocProOH (0.71 g.) and HPhe-MePheOMe (1.13 g.) by the mixed anhydride method using diphenylphosphinic chloride gave BocPro-Phe-MePheOMe in 73% yield. Hydrazinolysis of BocPro-Phe-MePheOMe (3.10 g.) gave BocPro-Phe-MePheNHNH$_2$ in 84% yield.

Condensation of BocPro-Phe-MePheNHNH$_2$ (0.86 g.) and HSar-Leu-MetNH$_2$ (Example 3, 0.63 g.) by the acyl azide method (Yajima et al., Chem. Pharm. Bull., vol. 19, p. 1900, 1971) gave BocPro-Phe-MePhe-Sar-Leu-MetNH$_2$ in 75% yield. De-t-butoxycarbonylation of BocPro-Phe-MePhe-Sar-Leu-MetNH$_2$ (0.90 g.) using trifluoroacetic acid in methylene dichloride gave HPro-Phe-MePhe-Gly-Leu-MetNH$_2$, which was isolated as the amorphous white solid phosphate (1:1) salt in 59% yield.

EXAMPLE 12

HPro-DPhe-Phe-DTrp-Leu-MetNH$_2$

Condensation of BocTrpOPFP (1.41 g.) and HLeu-Met-NH$_2$ hydrochloride salt (Example 1, 0.89 g.) by the activated ester method gave BocTrp-Leu-MetNH$_2$ in 81% yield. De-t-butoxycarbonylation of BocTrp-Leu-MetNH$_2$ (1.06 g.) using trifluoroacetic acid containing 10% water gave Htrp-Leu-MetNH$_2$ in 81% yield.

Condensation of BocPro-DPhe-PheNHNH$_2$ (Example 9, 477 mg.) and HTrp-Leu-MetNH$_2$ (510 mg.) by the acyl azide method (Yajima et al., Chem. Pharm. Bull., vol. 19, p. 1900, 1971) gave BocPro-DPhe-Phe-Trp-Leu-MetNH$_2$ in 97% yield. De-t-butoxycarbonylation of BocPro-DPhe-Phe-Trp-Leu-MetNH$_2$ (0.80 g.) using trifluoroacetic acid containing 10% water gave HPro-DPhe-Phe-DTrp-Leu-MetNh$_2$, which was isolated as the amorphous white solid phosphate (1:2) salt tetrahydrate in 32% yield.

EXAMPLE 13

HPro-Phe-Phe-LDap-Leu-MetNH$_2$

Condensation of ZPheOSu (6.96 g.) and HLDap(Boc)OH (6.0 g.) by the salt coupling method gave ZPhe-LDap(Boc)OH in 64% yield. Condensation of ZPhe-LDap(Boc)OH (4.85 g.) and HLeuOMe (2.73 g.) by the mixed anhydride method using diphenylphosphinic chloride gave ZPhe-LDap(Boc)-LeuOMe in 69% yield. Debenzyloxycarbonylation of ZPhe-LDap(Boc)-LeuOMe (4.15 g.) by hydrogenation with palladium catalyst gave HPhe-LDap(Boc)-LeuOMe in 100% yield. Condensation of BocPro-PheOH (1.09 g.) and HPhe-LDap(Boc)-LeuOMe (1.44 g.) using dicyclohexylcarbodiimide and N-hydroxynorbornenedicarboximide gave BocPro-Phe-Phe-LDap(Boc)-LeuOMe in 75% yield. Hydrazinolysis of BocPro-Phe-Phe-LDap(Boc)-LeuOMe (1.69 g.) gave BocPro-Phe-Phe-LDap(Boc)-LeuNHNH$_2$ in 36% yield.

Condensation of BocPro-Phe-Phe-LDap(Boc)-LeuNHNH$_2$ (607 mg.) and HMetNH$_2$ (150 mg.) by the acyl azide method (Yajima et al., Chem. Pharm. Bull., vol. 19, p. 1900, 1971) gave BocPro-Phe-Phe-LDap(Boc)-Leu-MetNH$_2$ in 67% yield. De-t-butoxycarbonylation of BocPro-Phe-Phe-LDap(Boc)-Leu-MetNH$_2$ (430 mg.) using hydrogen chloride in acetic acid gave HPro-Phe-Phe-LDap-Leu-MetNH$_2$, which was isolated as the amorphous white solid phosphate (1:2) salt dihydrate in 95% yield.

EXAMPLE 14

HPro-Phe-Phe-CabLeu-MetNH$_2$

BocCabLeuOMe was prepared by treating the sulfonium methyl iodide derivative of BocMet-LeuOMe with sodium hydride as described by Freidinger et al. (J. Org. Chem., vol. 47, pp. 104–109, 1982), who obtained BocCabLeuOH instead of BocCabLeuOMe by this method. Hydrazinolysis of BocCabLeuOMe (8.7 g.) gave BocCabLeuNHNH$_2$ in 47% yield. Condensation of BocCabLeuNHNH$_2$ (3.3. g.) and HMetNH$_2$ hydrochloride salt (1.85 g.) by the acyl azide method (Yajima et al., Chem. Pharm. Bull., vol. 19, p. 1900, 1971) gave BocCabLeu-MetNH$_2$ in 43% yield. De-t-butoxycarbonylation of BocCabLeu-MetNH$_2$ (1.67 g.) using hydrogen chloride in ethyl acetate gave HCabLeu-MetNH$_2$ in 93% yield.

Condensation of BocPro-Phe-PheNHNH$_2$ (Example 1, 1.57 g.) and HCabLeu-MetNH$_2$ (1.15 g.) by the acyl azide method (Yajima et al., Chem. Pharm. Bull., vol. 19, p. 1900, 1971) gave BocPro-Phe-Phe-CabLeu-MetNH$_2$ in 36% yield. De-t-butoxycarbonylation of BocPro-Phe-Phe-CabLeu-MetNH$_2$ (830 mg.) using hydrogen chloride in ethyl acetate gave HPro-Phe-Phe-CabLeu-MetNH$_2$, which was isolated as the amorphous white solid hydrochloride salt in 62% yield.

EXAMPLE 15

HPro-Phe-Phe-Glu-Leu-MetNH$_2$

Condensation of ZPheOH (3.00 g.) and HGlu(tBu)OMe hydrochloride salt (2.54 g.) by the mixed anhydride method using isobutyl chloroformate gave ZPhe-Glu(tBu)OMe in 88% yield. Debenzyloxycarbonylation of ZPhe-Glu(tBu)OMe (4.30 g.) by hydrogenation with palladium catalyst gave HPhe-Glu(tBu)OMe, which was not isolated but immediately condensed with BocPro-PheOH (3.12 g.) using dicyclohexylcarbodiimide and hydroxysuccinimide, affording BocPro-Phe-Phe-Glu(tBu)OMe in 22% yield. Hydrazinolysis of BocPro-Phe-Phe-Glu(tBu)OMe (1.09 g.) gave BocPro-Phe-Phe-Glu(tBu)NHNH$_2$ in 58% yield.

Condensation of BocPro-Phe-Phe-Glu(tBu)NHNH$_2$ (0.570 g.) and HLeu-MetNH$_2$ hydrochloride salt (Example 1, 0.560 g.) by the acyl azide method (Yajima et al., Chem. Pharm. Bull., vol. 19, p. 1900, 1971) have BocPro-Phe-Phe-Glu(tBu)-Leu-MetNH$_2$ in 77% yield. De-t-butylation and de-t-butoxycarbonylation of BocPro-Phe-Phe-Glu(tBu)-Leu-MetNH$_2$ using hydrogen chloride in acetic acid gave HPro-Phe-Phe-Glu-Leu-MetNH₂, which was isolated as the amorphous off-white solid hydrochloride salt in 38% yield.

EXAMPLE 16

HPro-Phe-Phe-Gly-Gal-MetNH₂

Condensation of BocPro-PheOH (3.12 g.) and HPhe-Gly-OBz (3.50 g.) using dicyclohexylcarbodiimide and N-hydroxynorbornenedicarboximide gave BocPro-Phe-Phe-GlyOBz in 66% yield. Debenzylation of Boc-Pro-Phe-Phe-GlyOBz (3.70 g.) by hydrogenation with palladium catalyst gave BocPro-Phe-Phe-GlyOH in 100% yield.

Condensation of BocGalOH (1.22 g.) and HMetNH₂ (1.45 g.) by the mixed anhydride method using isobutyl chloroformate gave BocGal-MetNH₂ in 55% yield. De-t-butoxycarbonylation of BocGal-MetNH₂ (0.70 g.) using hydrogen chloride in acetic acid gave HGal-MetNH₂ in 57% yield.

Condensation of BocPro-Phe-Phe-GlyOH (1.61 g.) and HGal-MetNH₂ dihydrochloride salt (0.70 g.) using dicyclohexylcarbodiimide and 4-dimethylaminopyridine as catalyst gave BocPro-Phe-Phe-Gly-Gal-MetNH₂ in 28% yield. De-t-butoxycarbonylation of BocPro-Phe-Phe-Gly-Gal-MetNH₂ (0.44 g.) using hydrogen chloride in acetic acid gave HPro-Phe-Phe-Gly-Gal-MetNH₂, which was isolated as the amorphous white solid dihydrochloride acetate salt hydrate in 35% yield.

EXAMPLE 17

HPro-DTrp-Phe-DTrp-Leu-MetNH₂

Two methods designated A and B are described for the preparation of this compound. Method B is the preferred method and is described in greater detail.

A. Condensation of BocDTrpOPFP (7.06 g.) and HPheOMe hydrochloride salt (3.24 g.) by the activated ester method gave BocDTrp-PheOMe in 81% yield. De-t-butoxycarbonylation of BocDTrp-PheOMe (5.0 g.) using trifluoroacetic acid gave HDTrp-PheOMe trifluoroacetate salt in 61% yield. Condensation of Boc-ProOPFP (2.23 g.) and HDTrp-PheOMe trifluoroacetate salt (2.75 g.) by the activated ester method gave BocPro-DTrp-PheOMe in 74% yield. Hydrazinolysis of BocPro-DTrp-PheOMe (2.00 g.) gave BocPro-DTrp-PheNHNH₂ yield.

Condensation of BocDTrpOPFP (2.35 g.) and HLeu-MetNH₂ hydrochloride salt (Example 1, 1.49 g.) by the activated ester method gave BocDTrp-Leu-MetNH₂ in 71% yield. De-t-butoxycarbonylation of BocDTrp-Leu-MetNH₂ (1.75 g.) using trifluoroacetic acid gave HDTrp-Leu-MetNH₂ trifluoroacetate salt in 50% yield.

Condensation of BocPro-Dtrp-PheNHNH₂ (0.861 g.) and HDTrp-Leu-MetNH₂ trifluoroacetate salt (0.860 g.) by the acyl azide method (Yajima et al., Chem. Pharm. Bull., vol. 19, p. 1900, 1971) gave BocPro-DTrp-Phe-DTrp-Leu-MetNH₂ in 60% yield. De-t-butoxycarbonylation of BocPro-DTrp-Phe-DTrp-Leu-MetNH₂ (0.875 g.) using trifluoroacetic acid in methyl ethyl sulfide and ethane dithiol gave HPro-DTrp-Phe-DTrp-Leu-MetNH₂, which was isolated as the amorphous white solid phosphate (1:1) salt hydrate (2:5) in 33% yield.

B. A chilled mixture of BocProOSu (96.1 mmole.) and dimethylformamide (100 ml.) was added with cooling to 0° C. to a solution of HDTrpOH (0.1 mole) and potassium hydroxide (85%, 0.1 mole) in dimethylformamide (150 ml.) and water (25 ml.). The mixture was stirred for one hour at 0° C., allowed to warm to room temperature overnight, and stripped of volatiles. The residue was partitioned between ethyl acetate and aqueous citric acid (5%). Crystals which formed between the layers were collected by filtration and recrystallized from methanol-water. More product was obtained by stripping the ethyl acetate layer of ethyl acetate and recrystallizing the residue from methanol-water. The recrystallizates were combined, affording BocProD-TrpOH in 86% yield (33.1 g., m.r. 210°–213° C.).

To a solution of BocPro-DTrpOH (74.7 mmole.) and HPheOBz p-toluenesulfonate salt (75.0 mmole.) in tetrahydrofuran (300 ml.) chilled to 0° C. were added first ethyldiisopropylamine (150 mmole.), then 1-hydroxybenzotriazole (75.0 mmole.), then dicyclohexylcarbodiimide (75.0 mmole.). The mixture was allowed to warm to room temperature overnight, filtered and stripped of volatiles. A solution of the residue in ethyl acetate was washed with aqueous citric acid (5%), water, saturated aqueous sodium bicarbonate and saturated aqueous sodium chloride, dried over magnesium sulfate, filtered and stripped of volatiles. A mixture of the residue with ether and hexane, which failed to induce crystallization, was stripped of volatiles, affording BocPro-DTrp-PheOBz in 10% yield as a foam (48.2 g.).

A mixture of palladium on carbon (10%, 4.0 g.) in ethanol (20 ml.) was added to a solution of BocPro-DTrp-PheOBz (70.44 mmole.) in methanol (100 ml.). The mixture was diluted to 200 ml. with methanol, hydrogenated under pressure for three hours and filtered. The filtrate was stripped of volatiles. After unsuccessful attempts to crystallize the residue from ether-hexane and methanol-water it was twice dissolved in, and stripped of, chloroform and dried under high vacuum, affording BocPro-DTrp-PheOH in 95% yield as a foam (36.6 g.).

Solutions of leucine (90.0 mmole.) in dimethylformamide (150 ml.) and potassium hydroxide (90.0 mmole.) in water (25 ml.) were combined and chilled in an ice-salt bath. A chilled mixture of BocDTrpOSu (89.7 mmole.) in dimethylformamide (100 ml.) was then added. The mixture was stirred for one hour at the ice-salt bath temperature, allowed to warm to room temperature overnight, and distributed between aqueous citric acid (5%) and ether. The aqueous layer was extracted twice more with ether. The ethereal extracts were combined and dried over magnesium sulfate. The product precipitated from the ether onto the drying agent. Ether was removed from the mixture. Extraction of the solids with methanol, removal of the methanol and recrystallization of the residue from methanol-water afforded BocDTrp-LeuOH in 74% yield (27.85 g., m.r. 187°–190° C.).

Triethylamine (120 mmole.), then 1-hydroxybenzotriazole (60.0 mmole.), then dicyclohexylcarbodiimide (60.0 mmole.) were added with stirring to a solution of BocDTrp-LeuOH (59.9 mmole.) and HMetNH₂ hydrochloride salt (60.0 mmole.) in tetrahydrofuran (300 ml.) with cooling to 0° C. Stirring was continued at 0° C. for one hour, then overnight while the mixture was allowed to warm to room temperature. The mixture was filtered and the filtrate was stripped of volatiles. Crystallization of the residue from isopropyl acetate affording BocDTrp-Leu-MetNH₂ in 80% yield (26.3 g., m.r. 190°–194° C.).

BocDTrp-Leu-MetNH$_2$ (47.5 mmole) was added to a solution of trifluoroacetic acid (230 ml.), dimethylsulfide (260 ml.) and ethanedithiol (20 ml.) with cooling to 0° C. The mixture was allowed to warm to room temperature during one and one half hours, then stripped of volatiles. Attempted crystallization of the residue from ethyl acetate-hexane was unsuccessful, and the mixture was stripped again. The residue was dissolved in methanol-ether. Removal of a small amount (about 300 mg.) of solid and addition of acetic acid to the filtrate afforded HDTrp-Leu-MetNH$_2$ acetate salt in 60% yield (12.6 g., m.r. 154°-160° C.).

1-Hydroxybenzotriazole (5.00 mmole.) and dicyclohexylcarbodiimide (5.00 mmole) were added with stirring and cooling to 0° C. to a solution of BocPro-DTrp-PheOH (4.93 mmole.). HDTrp-Leu-MetNH$_2$ acetate salt (4.93 mmole) and ethyldiisopropylamine (10.00 mmole.) in tetrahydrofuran (50 ml.). The mixture was allowed to warm to room temperature overnight with continued stirring, then filtered. The filtrate was stripped of volatiles. Purification of the residue by high pressure liquid chromatography on silica gel using ethyl acetate/isopropyl alcohol (95:5) as eluant and recrystallization from isopropyl acetate gave BocPro-DTrp-Phe-DTrp-Leu-MMetNH$_2$ in 57% yield in two crops (2.1 g., m.r. 119°-130° C.; 640 mg.).

BocPro-DTrp-Phe-DTrp-Leu-MetNH$_2$ (2.45 mmole.) was added to a solution of trifluoroacetic acid (18 ml.), dimethylsulfide (20 ml.) and ethanedithiol (1.8 ml.) with cooling to 0° C. The mixture was allowed to warm to room temperature, stirred for one hour, and stripped of volatiles. The residue was washed with hexane, then with ether, then purified by reverse phase high pressure liquid chromatography on octadecylsilated silica gel using methanol-water (75:25) containing ammonium acetate (0.2%) as eluant. Conversion of the product to the phosphate salt by ion exchange and lyophilization afforded HPro-DTrp-Phe-DTrp-Leu-MetNH$_2$, which was isolated as the amorphous white solid phosphate (1:1) salt hydrate (2:7) in 62% yield (1.63 g.).

EXAMPLE 18

HPro-Phe-D,LBpa-Gly-Leu-MetNH$_2$

Condensation of BocGlyOPFP (7.2 g.) and HLeu-MetNH$_2$ hydrochloride salt (Example 1, 10.2 g.) by the actived ester method gave BocGly-Leu-MetNH$_2$ in 73% yield. De-t-butoxycarbonylation of BocGly-Leu-MetNH$_2$ (9.38 g.) using hydrogen chloride in acetic acid gave HGly-Leu-MetNH$_2$ in 77% yield. Condensation of BocD,LBpaOH (1.6 g.) and H-Gly-Leu-MetNH$_2$ (2.13 g.) by the mixed anhydride method using diphenylphosphinyl chloride gave BocD,LBpa-Gly-Leu-MetNH$_2$, de-t-butoxycarbonylation of which (1.1 g.) using hydrogen chloride in acetic acid gave HD, LBpa-Gly-Leu-MetNH$_2$ in 30% overall yield.

Condensation of BocPro-PheOH (543 mg.) and HD,LBpaGly-Leu-MetNH$_2$ (530 mg.) using dicyclohexylcarbodiimide and N-hydroxysuccinimide gave BocPro-Phe-D,LBpa-Gly-Leu-MetNH$_2$ in 100% yield. De-t-butoxycarbonylation of BocPro-Phe-D,LBpa-Gly-Leu-MetNH$_2$ (1.2 g.) using hydrogen chloride in acetic acid gave HPro-Phe-D,LBpa-Gly-Leu-MetNH$_2$, which was isolated as the amorphous white solid dihydrochloride salt hydrate (2:5) in 41% yield.

EXAMPLES 19-20

HPro-Phe-Phe-LBpa-Leu-MetNH$_2$

HPro-Phe-Phe-DBpa-Leu-MetNH$_2$

Condensation of ZPheOH (29.2 g.) and HPheOMe (21.6 g.) by the mixed anhydride method using isobutyl chloroformate gave ZPhe-PHeOMe in 57% yield. Debenzyloxycarbonylation of ZPhe-PHeOMe (26.4 g.) by hydrogenation in acidified methanol with palladium catalyst gave HPhe-PheOMe in 86% yield. Condensation of BocProOH (6.46 g.) and HPhe-PheOMe hydrochloride (10.9 g.) by the mixed anhydride method using diphenylphosphinyl chloride gave BocPro-Phe-PheOMe in 67% yield. Hydrazinolysis of BocPro-Phe-PheOMe (9.57 g.) gave BocPro-Phe-Phe-NHNH$_2$ in 92% yield.

Condensation of BocBpaOH (2.7 g.) and HLeu-MetNH$_2$ hydrochloride salt (Example 1, 3.0 g.) by the mixed anhydride method using diphenylphosphinyl chloride gave BocBpa-Leu-MetNH$_2$ in 50% yield. De-t-butoxycarbonylation of BocBpa-Leu-MetNH$_2$ (2.6 g.) using hydrogen chloride in acetic acid gave HBpa-Leu-MetNH$_2$ in 100% yield.

Condensation of BocPro-Phe-PheNHNH$_2$ (2.83 g.) and HBpa-Leu-MetNH$_2$ (2.61 g.) by the azide coupling method (Yajima et al., Chem. Pharm. Bull., vol. 19, p. 1900, 1971) gave BocPro-Phe-Phe-Bpa-Leu-MetNH$_2$ in 68% yield. The diastereoisomers were separated by column chromatography on silica gel using chloroform-methanol (96:4) as eluant. Separate de-t-butoxycarbonylation of each isomer using hydrogen chloride in acetic acid gave HPro-Phe-Phe-LBpa-Leu-MetNH$_2$ as the amorphous white solid dihydrochloride salt tetrahydrate in 79% yield and HPro-Phe-Phe-DBpa-Leu-MetNH$_2$ as the amorphous white solid dihydrochloride salt hydrate (2:7) in 91% yield.

EXAMPLES 21-22

HPro-DPhe-LBpa-DTrp-Leu-MetNH$_2$

HPro-DPhe-DBpa-DTrp-Leu-MetNH$_2$

Condensation of BocDTrpOPFP (4.70 g.) and HLeu-MetNH$_2$ hydrochloride salt (Example 1, 2.98 g.) by the activated ester method using ethyldiisopropylamine gave BocDTrp-Leu-MetNH$_2$ in 71% yield. De-t-butoxycarbonylation of BocDTrp-Leu-MetNH$_2$ using trifluoroacetic acid, methyl sulfide, and ethanedithiol gave HDTrp-Leu-MetNH$_2$ trifluoroacetate salt in 100% yield. Condensation of BocD,LBpaOH (2.95 g.) and HDTrp-Leu-MetNH$_2$ trifluoroacetate salt (3.79 g.) by the mixed anhydride method using diphenylphosphinyl chloride and separation of the diastereoisomers by column chromatography on silica gel using chloroform-methanol (91:9) as eluant gave BocLBpa-DTrp-Leu-MetNH$_2$ and BocDBpa-DTrp-Leu-MetNH$_2$ each in 19% yield. De-t-butoxycarbonylation of BocLBpa-DTrp-Leu-MetNH$_2$ (0.875 g.) and BocLBpa-DTrp-Leu-MetNH$_2$ (0.875 g.) using trifluroracetic acid in methyl ethyl sulfide and ethanedithiol gave HLBpa-DTrp-Leu-MetNH$_2$ and HDBpa-DTrp-Leu-MetNH$_2$, both as the trifluoroacetate salts and both in 100% yield.

Condensation of BocPro-DPheOH (Example 9, 0.490 g., 0.490 g.) with each of HLBpa-DTrp-Leu-MetNH$_2$ di-trifluoroacetate salt (1.04 g.) and HDBpa-DTrp-Leu-MetNH$_2$ di-trifluoroacetate salt (1.04 g.) using dicyclohexylcarbodiimide and N-hydroxysuccinimide gave BocPro-DPhe-LBpa-DTrp-Leu-MetNH₂ in 66% yield and BocPro-DPhe-DBpa-DTrp-Leu-MetNH₂ in 46% yield. De-t-butoxycarbonylation of BocPro-DPhe-LBpa-DTrp-Leu-MetNH₂ (0.700 g.) and BocPro-DPhe-DBpa-DTrp-Leu-MetNH₂ (0.475 g.) using trifluoroacetic acid in methyl ethyl sulfide and ethanedithiol gave HPro-DPhe-LBpa-DTrp-Leu-MetNH₂, which was isolated as the amorphous white solid phosphate (2:3) salt hydrate (2:5), and HPro-DPhe-DBpa-DTrp-Leu-MetNH₂ which was isolated as the amorphous white solid phosphate (2:3) salt trihydrate, both in 37% yield.

EXAMPLE 23

HPro-DPhe-Phe-DPhe-Leu-MetNH₂

Condensation of ZDPheOH (12 g.) and HPheOMe hydrochloride salt (8.6 g.) by the mixed anhydride method using isobutyl chloroformate gave ZDPhe-PheOMe in 92% yield. Debenzyloxycarbonylation of ZDPhe-PheOMe (12.85 g.) by hydrogenation with palladium catalyst gave HDPhe-PheOMe in 95% yield. Condensation of BocProOPFP (3.89 g.) and HDPhe-PheOMe (3.87 g.) by the activated ester method gave BocPro-DPhe-PheOMe in 54% yield. Hydrazinolysis of BocPro-DPhe-PheOMe (2.62 g.) gave BocPro-DPhe-PheNHNH₂ in 90% yield.

Condensation of BocDPheOH (2.65 g.) and HLeu-MetNH₂ hydrochloride salt (Example 1, 2.98 g.) by the mixed anhydride method using isobutyl chloroformate gave BocDPhe-Leu-MetNH₂ in 57% yield. De-t-butoxycarbonylation of BocDPhe-Leu-MetNH₂ (2.7 g.) using hydrogen chloride in ethyl acetate gave HDPhe-Leu-MetNH₂ hydrochloride salt in 82% yield.

Condensation of BocPro-DPhe-PheNHNH₂ (2.09 g.) and HDPhe-Leu-MetNH₂ hydrochloride salt (1.78 g.) by the acyl azide method (Yajima et al., Chem. Pharm. Bull., vol. 19, p. 1900, 1971) gave BocPro-DPhe-Phe-DPhe-Leu-MetNH₂ in 91% yield. De-t-butoxycarbonylation of BocPro-DPhe-Phe-DPhe-Leu-MetNH₂ (2.32 g.) using hydrogen chloride in ethyl acetate gave HPro-DPhe-Phe-DPhe-Leu-MetNH₂, which was isolated as the amorphous white solid phosphate (1:1) salt dihydrate in 44% yield.

EXAMPLES 24-25

HPro-LBpa-Phe-DPhe-Leu-MetNH₂

HPro-DBpa-Phe-DPhe-Leu-MetNH₂

Condensation of BocD,LBpaOH (5.32 g.) and HPheOMe hydrochloride salt (4.31 g.) by the mixed anhydride method using diphenylphosphinyl chloride gave BocD,LBpa-PheOMe. The diastereoisomers were separated by fractional crystallization in yields of 20% (L-isomer) and 6% (D-isomer). De-t-butoxycarbonylation of BocLBpa-PheOMe (1.50 g.) and BocDBpa-PheOMe (0.500 g.) using hydrogen chloride in ethyl acetate gave HLBpa-PheOMe in 98% yield and HDBpa-PheOMe in 100% yield. Condensation of BocProOPFP (2.53 g., 0.808 g.) with each of HLBpa-PheOMe (1.33 g.) and HDBpa-PheOMe (0.425 g.) by the activated ester method gave BocPro-LBpa-PheOMe in 76% yield and BocPro-DBpa-PheOMe in 92% yield. Hydrazinolysis of BocPro-LBpa-PheOMe (1.20 g.) and Boc Pro-DBpa-PheOMe (0.500 g.) gave BocPro-LBpa-PheNHNH₂ and BocPro-DBpa-PheNHNH₂, both in 100% yield.

Condensation of each of BocPro-LBpa-PheNHNH₂ (1.20 g.) and BocPro-DBpa-PheNHNH₂ (0.450 g.) with HDPhe-Leu-MetNH₂ hydrochloride salt (Example 23, 1.02 g., 0.445 g.) by the acyl azide method (Yajima et al., Chem. Pharm. Bull., vol. 19, p. 1900, 1971) gave BocPro-LBpa-Phe-DPhe-Leu-MetNH₂ in 51% yield and BocPro-DBpa-Phe-DPhe-Leu-MetNH₂ in 44% yield. De-t-butoxycarbonylation of BocPro-LBpa-Phe-DPhe-Leu-MetNH₂ (0.500 g.) and BocPro-DBpa-Phe-DPhe-Leu-MetNH₂ (0.250 g.) using hydrogen chloride in dioxane gave HPro-LBpa-Phe-DPhe-Leu-MetHN₂, which was isolated as the amorphous white solid dihydrochloride salt hydrate (2:9) in 53% yield, and HPro-DBpa-Phe-DPhe-Leu-MetNH₂, which was isolated as the dihydrochloride salt hexahydrate in 59% yield.

EXAMPLES 26-27

HPro-Phe-DBpa-Gly-Leu-MetNH₂

HPro-Phe-LBpa-Gly-Leu-MetNH₂

Separation of HPro-Phe-D,LBpa-Gly-Leu-MetNH₂ dihydrochloride salt hydrate (5:2) (Example 18, 240 mg.) first by column chromatography on silica gel using ethyl acetate-pyridine-acetic acid-water (150:54:16:30) as eluant and then by reverse phase high pressure liquid chromatography on octadecylsilated silica gel using methanol-water (55:45) containing ammonium acetate (0.2%) as eluant gave HPro-Phe-DBpa-Gly-Leu-MetNH₂, which was isolated as the dihydrochloride salt trihydrate, and HPro-Phe-LBpa-Gly-Leu-MetNH₂, which was isolated as the dihydrochloride salt dihydrate.

EXAMPLE 28

HPro-DPhg-Phe-DPhe-Leu-MetNH₂

Condensation of BocDPhgOH (5.0 g.) and HPheOMe hydrochloride salt (4.3 g.) by the mixed anhydride method using isobutyl chloroformate gave BocDPhg-PheOMe in 98% yield. De-t-butoxycarbonylation of BocDPhg-PheOMe (4.23 g.) using hydrogen chloride in ethyl acetate gave HDPhg-PheOMe in 100% yield. Condensation of BocProOPFP (3.81 g.) and HDPhg-PheOMe hydrochloride salt (3.5 g.) by the activated ester method gave BocPro-DPhg-PheOMe in 74% yield. Hydrazinolysis of Bocpro-DPhg-PheOMe (3.57 g.) gave BocPro-DPhg-PheNHNH₂ in 80% yield.

Condensation of BocPro-DPhg-PheNHNH₂ (1.27 g.) and HDPhe-Leu-MetNH₂ hydrochloride salt (Example 23, 1.11 g.) by the acyl azide method (Yajima et al., Chem. Pharm. Bull., vol. 19, p. 1900, 1971) gave BocPro-DPhg-Phe-DPhe-Leu-MetNH₂ in 89% yield. De-t-butoxycarbonylation of BocPro-DPhg-Phe-DPhe-Leu-MetNH₂ (1.67 g.) using hydrogen chloride in ethyl acetate gave HPro-DPhg-Phe-DPhe-Leu-MetNH₂, which was isolated as the amorphous white solid phosphate (1:1) salt pentahydrate in 12% yield.

EXAMPLE 29

HPro-DPhe-Hfe-DPhe-Leu-MetNH₂

Condensation of BocPro-DPheOH (Example 9, 1.50 g.) and HHfeOMe hydrochloride salt (0.950 g.) by the mixed anhydride method using diphenylphosphinyl chloride gave BocPro-DPhe-HfeOMe in 71% yield. Hydrazinolysis of BocPro-DPhe-HfeOMe (1.30 g.) gave BocPro-DPhe-HfeNHNH₂ in 91% yield.

Condensation of BocPro-DPhe-HfeNHNH₂ (0.930 g.) and HDPhe-Leu-MetNH₂ hydrochloride salt (Example 23, 0.445 g.) by the acyl azide method (Yajima et al., Chem. Pharm. Bull., vol. 19, p. 1900, 1971) gave BocPro-DPhe-Hfe-DPhe-Leu-MetNH₂ in 69% yield. De-t-butoxycarbonylation of BocPro-DPhe-Hfe-DPhe-Leu-MetNH₂ (0.500 g.) using hydrogen chloride in acetic acid gave HPro-DPhe-Hfe-DPhe-Leu-MetNH₂, which was isolated as the amorphous white solid hydrochloride diacetate salt pentahydrate in 21% yield.

EXAMPLE 30

HPro-DPhe-Bgl-DPhe-Leu-MetNH₂

Condensation of BocPro-DPheOH (Example 9, 725 mg.) and HBglOEt (387 mg.) using dicyclohexylcarbodiimide and N-hydroxysuccinimide gave BocPro-DPhe-BglOEt in 66% yield. Hydrazinolysis of BocPro-DPhe-BglOEt (550 mg.) gave BocPro-DPhe-BglNHNH₂ in 63% yield.

Condensation of BocPro-DPhe-BglNHNH₂ (320 mg.) and HDPhe-Leu-MetNH₂ hydrochloride salt (Example 23, 271 mg.) by the acyl azide method (Yajima et al., Chem. Pharm. Bull, vol. 19, p. 1900, 1971) gave BocPro-DPhe-Bgl-DPhe-Leu-MetNH₂ in 58% yield. De-t-butoxycarbonylation of BocPro-DPhe-Bgl-DPhe-Leu-MetNH₂ (310 mg.) using hydrogen chloride in acetic acid gave Hpro-DPhe-Bgl-DPhe-Leu-MetNH₂, which was isolated as the amorphous white solid hydrochloride salt dihydrate in 86% yiled.

EXAMPLE 31

HPro-DPhe-Phe-DPhe-Leu-NleNH₂

Condensation of BocDPheOH (2.65 g.) and HLeuOBz hydrobromide salt (3.02 g.) by the mixed anhydride method using diphenylphosphinyl chloride gave BocDPhe-LeuOBz in 54% yield. Debenzylation of BocDPhe-LeuOBz (2.25 g.) by hydrogenation with palladium catalyst gave BocDPhe-LeuOH in 87% yield. Condensation of BocDPhe-LeuOH (1.50 g.) and HNleNH₂ hydrochloride salt (0.667 g.) using dicyclohexylcarbodiimide and N-hydroxysuccinimide gave BocDPhe-Leu-NleNH₂ in 60% yield. De-t-butoxycarbonylation of BocDPhe-Leu-NleNH₂ (1.00 g.) using hydrogen chloride in acetic acid gave HDPhe-Leu-NleNH₂ hydrochloride salt in 79% yield.

Condensation of BocPro-DPhe-PheNHNH₂ (Example 23, 0.717 g.) and HDPhe-Leu-NleNH₂ hydrochloride salt (0.585 g.) by the acyl azide method (Yajima et al., Chem. Pharm. Bull., vol. 19, p. 1900, 1971) gave BocPro-DPhe-Phe-DPhe-Leu-NleNH₂ in 51% yield. De-t-butoxycarbonylation of BocPro-Dphe-Dphe-Leu-NleNH₂ (0.500 g.) using hydrogen chloride in acetic acid gave HPro-DPhe-Phe-DPhe-Leu-NleNH₂, which was isolated as the amorphous white solid hydrochloride salt trihydrate in 36% yield.

EXAMPLE 32

HPro-DPhe-Pgl-DPhe-Leu-MetNH₂

Condensation of BocPro-DPheOH (Example 9, 1.45 g.) and HPglOEt (0.83 g.) using dicyclohexylcarbodiimide and N-hydroxysuccinimide gave BocPro-DPhe-PglOEt in 59% yield. Hydrazinolysis of BocPro-DPhe-PglOEt (1.23 g.) gave BocPro-DPhe-PglNHNH₂ in 100% yield.

Condensation of BocPro-DPhe-PglNHNH₂ (806 mg.) and HDPhe-Leu-MetNH₂ hydrochloride salt (Example 23, 668 mg.) by the acyl azide method (Yajima et al., Chem. Pharm. Bull., vol. 19, p. 1900, 1971) gave BocPro-DPhe-Pgl-DPhe-Leu-MetNH₂ in 68% yield. De-t-butoxycarbonylation of BocPro-DPhe-Pgl-DPhe-Leu-MetNH₂ (810 mg.) using hydrogen chloride in acetic acid gave HPro-DPhe-Pgl-DPhe-Leu-MetNH₂, which was isolated as the amorphous white solid hydrochloride salt trihydrate in 75% yield.

EXAMPLE 33

HPro-DTrp-Phe-DLys-Leu-MetNH₂

Demethylation of BocPro-DTrp-PheOMe (part A of Example 17, 1.25 g.) using aqueous sodium hydroxide gave BocPro-Dtrp-PheOH in 100% yield.

Condensation of FmocDLys(Boc)OH (1.00 g.) and HLeu-MetNH₂ hydrochloride salt (Example 1, 0.63 g.) using dicyclohexylcarbodiimide and 1-hydroxybenzotriazole gave FmocDLys(Boc)-Leu-MetNH₂ in 87% yield. De-9-fluorenylmethoxycarbonylation of FmocD-Lys(Boc)-Leu-MetNH₂ (1.00 g.) using piperidine in dimethylformamide gave HDLys(Boc)-Leu-MetNH₂ in 100% yield.

Condensation of BocPro-DTrp-PheOH (0.88 g.) and HDLys(Boc)-Leu-MetNH₂ (0.68 g.) using dicyclohexylcarbodiimide and 1-hydroxybenzotriazole gave BocPro-DTrp-Phe-DLys(Boc)-Leu-MetNH₂ in 46% yield. De-t-butoxycarbonylation of BocPro-DTrp-Phe-DLys(Boc)-Leu-MetNH₂ (560 mg.) using trifluoroacetic acid in dimethyl sulfide and ethanedithiol gave HPro-DTrp-Phe-DLys-Leu-MetNH₂, which was isolated as the amorphous white solid phosphate (1:1) acetate (1:3) salt in 26% yield.

EXAMPLE 34

HPro-DTrp-Phe-DArg-Leu-MetNH₂

Condensation of BocDArg(Tos)OH (2.14 g.) and HLeu-MetNH₂ hydrochloride salt (Example 1, 1.49 g.) using dicyclohexylcarbodiimide and 1-hydroxybenzotriazole gave BocDArg(Tos)-Leu-MetNH₂ in 54% yield. De-t-butoxycarbonylation of BocDArg(Tos)-Leu-MetNH₂ (1.7 g.) using hydrogen chloride in dioxane gave HDArg(Tos)-Leu-MetNH₂ in 45% yield.

Condensation of BocPro-DTrp-PheOH (Example 33, 658 mg.) and HDArg(Tos)-Leu-MetNH₂ (630 mg.) using dicyclohexylcarbodiimide and 1-hydroxybenzotriazole gave BocPro-DTrp-Phe-DArg(Tos)-Leu-MetNH₂ in 46% yield. De-t-butoxycarbonylation of BocPro-DTrp-Phe-DArg(Tos)-Leu-MetNH₂ (524 mg.) using trifluoroacetic acid in dimethyl sulfide and ethanedithiol gave HPro-DTrp-Phe-DArg(Tos)-Leu-MetNH₂ in 78% yield. De-p-toluenesulfonylation of HPro-DTrp-Phe-DArg(Tos)-Leu-MetNH₂ (420 mg.) using liquid hydrogen fluoride with anisole gave HPro-DTrp-Phe-DArg-Leu-MetNH₂, which was isolated as the amorphous off-white solid dihydrochloride acetate (2:1) salt hydrate (2:5) in 61% yield.

EXAMPLE 35

HPro-DTrp-Phe-DTrp-MeLeu-MetNH₂

Condensation of BocMeLeuOH (5.0 g.) and HMetNH₂ (3.7 g.) by the mixed anhydride method using diphenylphosphinyl chloride gave BocMeLeu-MetNH₂ in 67% yield. De-t-butoxycarbonylation of BocMeLeu-MetNH₂ (5.2 g.) using hydrogen chloride in ethyl acetate gave HMeLeu-MetNH₂ in 90% yield. Condensation of BocDTrpOPFP (5.60 g.) and HMeLeu-MetHN₂ (3.70 g.) by the activated ester method gave BocDTrp-MeLeu-MetNH₂ in 55% yield. De-t-butoxycarbonylation of BocDTrp-MeLeu-MetNH₂

(3.38 g.) using trifluoroacetic acid in dimethyl sulfide and ethanedithiol gave HDTrp-MeLeu-MetNH$_2$ in 74% yield.

Condensation of BocPro-DTrp-PheOH (Example 33, 1.65 g.) and HDTrp-MeLeu-MetNH$_2$ (1.34 g.) using dicyclohexylcarbodiimide and N-hydroxysuccinimide gave BocPro-DTrp-Phe-DTrp-MeLeu-MetNH$_2$ in 64% yield. De-t-butoxycarbonylation of BocPro-DTrp-Phe-DTrp-MeLeu-MetNH$_2$ (1.70 g.) using trifluoroacetic acid in dimethyl sulfide and ethanedithiol gave HPro-DTrp-Phe-DTrp-MeLeu-MetNH$_2$, which was isolated as the amorphous white solid phosphate (1:1) salt tetrahydrate in 67% yield.

EXAMPLE 36

HPro-DTrp-Phe-DTrp-Leu-MeMetNH$_2$

Condensation of BocLeuOH (5.00 g.) and HMe-MetNH$_2$ (4.00 g.) using dicyclohexylcarbodiimide and 1-hydroxybenzotriazole gave BocLeu-MeMetNH$_2$ in 81% yield. De-t-butoxycarbonylation of BocLeu-MeMetNH$_2$ (5.96 g.) using hydrogen chloride in ethyl acetate gave HLeu-MeMetNH$_2$ hydrochloride salt in 98% yield. Condensation of BocDTrpOPFP (7.56 g.) and HLeu-MeMetNH$_2$ hydrochloride salt (5.00 g.) by the activated ester method gave BocDTrp-Leu-MeMetNH$_2$ in 56% yield. De-t-butoxycarbonylation of BocDTrp-Leu-MeMetNH$_2$ (2.0 g.) using trifluoroacetic acid in dimethyl sulfide and ethanedithiol gave HDTrp-Leu-MeMetNH$_2$ trifluoroacetate salt in 79% yield.

Condensation of BocPro-DTrp-PheOH (Example 33, 1.49 g.) and HDTrp-Leu-MeMetNH$_2$ trifluoroacetate salt (1.25 g.) using dicyclohexylcarbodiimide and 1-hydroxybenzotriazole gave BocPro-DTrp-Phe-DTrp-Leu-MeMetNH$_2$ in 60% yield. De-t-butoxycarbonylation of BocPro-DTrp-Phe-DTrp-Leu-MeMetNH$_2$ (1.50 g.) using trifluoroacetic acid in dimethyl sulfide and ethanedithiol gave HPro-DTrp-Phe-DTrp-Leu-MeMetNH$_2$, which was isolated as the amorphous white solid phosphate (1:2) salt dihydrate in 57% yield.

EXAMPLE 37

HPro-Pcp-Pcp-Gly-Leu-MetNH$_2$

Condensation of BocProOH (7.00 g.) and HPcpOH (6.49 g.) using dicyclohexylcarbodiimide and N-hydroxysuccinimide gave BocPro-PcpOH in 50% yield. Condensation of BocPro-PcpOH (6.0 g.) and HPcpOMe (4.13 g.) using dicyclohexylcarbodiimide and N-hydroxysuccinimide gave BocPro-Pcp-PcpOMe in 62% yield. Demethylation of BocPro-Pcp-PcpOMe (1.25 g.) using aqueous sodium hydroxide gave BocPro-Pcp-PcpOH in 92% yield.

Condensation of BocPro-Pcp-PcpOH (1.00 g.) and HGly-Leu-MetNH$_2$ hydrochloride salt (0.639 g.) using dicyclohexylcarbodiimide and N-hydroxy-succinimide gave BocPro-Pcp-Pcp-Gly-Leu-MetNH$_2$ in 35% yield. De-t-butoxycarbonylation of BocPro-Pcp-Pcp-Gly-Leu-MetNH$_2$ (0.439 g.) using hydrogen chloride in acetic acid gave HPro-Pcp-Pcp-Gly-Leu-MetNH$_2$, which was isolated as the amorphous white solid hydrochloride salt sesquihydrate in 76% yield.

EXAMPLE 38

HPro-DTrp-MePhe-DTrp-Leu-MetNH$_2$

Condensation of BocDTrpOPFP (4.70 g.) and HMe-PheOBz hydrobromide salt (3.50 g.) by the activated ester method gave BocDTrp-MePheOBz in 69% yield. De-t-butoxycarbonylation of BocDTrp-MePHeOBz (3.50 g.) using trifluoroacetic acid in dimethyl sulfide and ethanedithiol gave HDTrp-MePheOBz in 100% yield. Condensation of BocProOPFP (2.44 g.) and HDTrp-MePHeOBz (3.59 g.) trifluoroacetate salt by the activated ester method gave BocPro-DTrp-MePHeOBz in 24% yield. Debenzylation of BocPro-DTrp-MePheOBz (0.930 g.) by hydrogenation with palladium catalyst gave BocPro-DTrp-MePheOH in 99% yield.

Condensation of BocPro-DTrp-MePheOH (0.800 g.) and HDTrp-Leu-MetNH$_2$ acetate salt (part B of Example 17, 0.721 g.) using dicyclohexylcarbodiimide and 1-hydroxybenzotriazole gave BocPro-DTrp-MePhe-DTrp-Leu-MetNH$_2$ in 31% yield. De-t-butoxycarbonylation of BocPro-DTrp-MePhe-DTrp-Leu-MetNH$_2$ (0.400 g.) using trifluoroacetic acid in dimethyl sulfide and ethanedithiol gave HPro-DTrp-MePhe-DTrp-Leu-MetNH$_2$, which was isolated as the amorphous white solid phosphate (1:2) salt dihydrate in 23% yield.

EXAMPLE 39

HPro-DTrp-Gly-DTrp-Leu-MetNH$_2$

Condensation of BocProOSu (6.00 g.) and HDTrpOH (4.08 g.) by the salt coupling method gave BocPro-DTrpOH in 70% yield. Condensation of BocPro-DTrpOH (2.93 g.) and HGlyOBz p-toluenesulfonate salt (2.47 g.) using dicyclohexylcarbodiimide and N-hydroxysuccinimide gave BocPro-DTrp-GlyOBz in 68% yield. Debenzylation of BocPro-DTrp-GlyOBz by hydrogenation with palladium catalyst gave BocPro-DTrp-GlyOH in 95% yield.

Condensation of BocDTrpOPFP (8.60 g.) and HLeu-MetNH$_2$ hydrochloride salt (Example 1, 5.44 g.) by the activated ester method gave BocDTrp-Leu-MetNH$_2$ in 67% yield. De-t-butoxycarbonylation of BocDTrp-Leu-MetNH$_2$ (6.69 g.) using trifluoroacetic acid in methyl ethyl sulfide and ethanedithiol gave HDTrp-Leu-MetNH$_2$ trifluoroacetate salt in 23% yield.

Condensation of BocPro-DTrp-GlyOH (1.00 g.) and HDTrp-Leu-MetNH$_2$ trifluoroacetate salt (1.10 g.) using dicyclohexylcarbodiimide and N-hydroxysuccinimide gave BocPro-DTrp-Gly-DTrp-Leu-MetNH$_2$ in 36% yield. De-t-butoxycarbonylation of BocPro-DTrp-Gly-DTrp-Leu-MetNH$_2$ (0.68 g.) using trifluoroacetic acid in methyl ethyl sulfide and ethanedithiol gave HPro-DTrp-Gly-DTrp-Leu-MetNH$_2$, which was isolated as the amorphous white solid phosphate (2:3) salt in 59% yield.

EXAMPLE 40

HPro-MePhe-Phe-Gly-Leu-MetNH$_2$

Condensation of BocProOH (4.30 g.) and HMe-PheOMe (2.74 L g.) by the mixed anhydride method using diphenylphosphinyl chloride gave BocPro-MePheOMe in 77% yield. Demethylation of BocPro-MePheOMe (3.0 g.) using aqueous sodium hydroxide gave BocPro-MePheOH in 83% yield. Condensation of BocPro-MePheOH (1.71 g.) and HPheOBz (2.14 g.) using dicyclohexylcarbodiimide and N-hydroxysuccinimide gave BocPro-MePhe-PheOBz in 76% yield. Debenzylation of BocPro-MePhe-PheOBz (2.0 g.) by hydrogenation with palladium catalyst gave BocPro-MePhe-PheOH in 100% yield.

Condensation of BocPro-MePhe-PheOH (670 mg.) and HGly-Leu-MetNH$_2$ (Example 7, 418 mg.) using dicyclohexylcarbodiimide and N-hydroxysuccinimide gave BocPro-MePhe-Phe-Gly-Leu-MetNH$_2$ in 50% yield. De-t-butoxycarbonylation of BocPro-MePhe-Phe-Gly-Leu-MetNH$_2$ (480 mg.) using hydrogen chloride in ethyl acetate gave HPro-MePhe-Phe-Bly-Leu-MetNH$_2$, which was isolated as the amorphous white solid hydrochloride salt monohydrate in 85% yield.

EXAMPLE 41

HPro-DTrp-Phe-MeDTrp-Leu-MetNH$_2$

Condensation of BocPro-DTrp-PheOH (Example 33, 2.63 g.) and HMeOTrpOMe hydrochloride (1.0 g.) using dicyclohexylcarbodiimide and 1-hydroxybenzotriazole gave BocPro-DTrp-Phe-MeDTrpOMe in 27% yield. Hydrazinolysis of BocPro-DTrp-Phe-MeDTrpOMe gave BocPro-DTrp-Phe-MeDTrpNHNH$_2$ in 92% yield.

Condensation of BocPro-DTrp-Phe-MeDTrpNHNH$_2$ (0.840 g.) and HLeu-MetNH$_2$ (0.328 g.) by the acyl azide method (Yajima et al., Chem. Pharm. Bull., vol. 19, p. 1900, 1971) gave BocPro-DTrp-Phe-MeDTrp-Leu-MetNH$_2$ in 57% yield. De-t-butoxycarbonylation of BocPro-DTrp-Phe-MeDTrp-Leu-MetNH$_2$ (0.450 g.) using trifluoroacetic acid in dimethyl sulfide and ethanedithiol gave HPro-DTrp-Phe-MeDTrp-Leu-MetNH$_2$, which was isolated as the crystalline white solid (m.r. 150°–175° C.) hydrochloride hydrate (3:2) in 59% yield.

EXAMPLE 42

HPro-DTrp-Phe-DTrp-Leu-MeNleNH$_2$

Condensation of BocDTrp-LeuOH (Example 38, 2.09 g.) and MeNleNH$_2$ (1.00 g.) using dicyclohexylcarbodiimide and 1-hydroxybenzotriazole gave BocDTrp-Leu-MeNleNH$_2$ in 99% yield. De-t-butoxycarbonylation of BocDTrp-Leu-MeNleNH$_2$ (2.50 g.) using trifluoroacetic acid in dimethyl sulfide and ethanedithiol gave HDTrp-Leu-MeNleNH$_2$ in 37% yield.

Condensation of BocPro-DTrp-PheOH (part B of Example 17, 0.700 g.) and HDTrp-Leu-MeNleNH$_2$ (0.520 g.) using dicyclohexylcarbodiimide and 1-hydroxybenzotriazole gave BocPro-DTrp-Phe-DTrp-Leu-MeNleNH$_2$ in 64% yield. De-t-butoxycarbonylation of BocPro-DTrp-Phe-DTrp-Leu-MeNleNH$_2$ (0.750 g.) using trifluoroacetic acid in dimethyl sulfide and ethanedithiol gave HPro-DTrp-Phe-DTrp-Leu-MeNleNH$_2$, which was isolated as the amorphous white solid phosphate (1:1) salt tetrahydrate in 30% yield.

EXAMPLE 43

HPro-MeDTrp-Phe-DTrp-Leu-MetNH$_2$

Condensation of BocProOH (4.63 g.) and MeDTrpOMe (5.00 g.) by the mixed anhydride method using diphenylphosphinyl chloride gave BocPro-MeDTrpOMe in 69% yield. Demethylation of BocPro-MeDTrpOMe (6.33 g.) using aqueous sodium hydroxide gave BocPro-MeDTrpOH in 77% yield. Condensation of BocPro-MeDTrpOH (3.60 g.) and HPheOBz (3.70 g.) using dicyclohexylcarbodiimide and N-hydroxysuccinimide gave BocPro-MeDTrp-PheOBz in 83% yield. Debenzylation of BocPro-MeDTrp-PheOBz (4.60 g.) by hydrogenation with palladium catalyst gave BocPro-MeDTrp-PheOH in 100% yield.

Condensation of BocPro-MeDTrp-PheOH (3.68 g.) and HDTrp-Leu-MetNH$_2$ acetate salt (part B of Example 17, 3.32 g.) using dicyclohexylcarbodiimide and N-hydroxysuccinimide gave BocPro-MeDTrp-Phe-DTrp-Leu-MetNH$_2$ in 20% yield. De-t-butoxycarbonylation of BocPro-MeDTrp-Phe-DTrp-Leu-MetNH$_2$ (1.00 g.) using trifluoroacetic acid in methyl ethyl sulfide and ethanedithiol gave HPro-MeDTrp-Phe-DTrp-Leu-MetNH$_2$, which was isolated as the amorphous white solid phosphate salt monohydrate in 67% yield.

BIOLOGICAL PROPERTIES OF THE COMPOUNDS

As stated above the hexapeptide amides of Formulas I–VIII are useful as Substance P agonists and/or antagonists and are therefore useful as analgesics and/or as antihypertensives. These utilities are shown by a test for tritiated substance P ($^3$H-SP) binding in rat submaxillary gland tissue or rat brain tissue, a test for SP agonist and antagonist effect in the guinea pig ileum, a test for SP antagonist effect in the rat vas deferens, and a test for protection against acetylcholine-induced writhing in the mouse.

Rat Submaxillary Gland or Brain Tissue $^3$H-SP Binding Test

Crude rat submaxillary gland or brain tissue is suspended in buffer containing protease inhibitors (and calcium ions and magnesium ions in the case of brain tissue) and incubated under nitrogen atmosphere with $^3$H-SP and test compound. The bound SP is then separated from free SP by filtration and quantitated by liquid scintillation spectroscopy. This test meets the criteria of reversibility, saturability, sensitivity to known SP agonists and antagonists, and specificity for an SP receptor binding assay.

With regard to reversibility, addition of unlabelled SP causes a gradual decrease in bound $^3$H-SP, showing that SP is not irreversibly bound to the receptors in the tissue. With regard to saturability, the amount of bound $^3$H-SP in the preparation increases in direct proportion to the concentration of $^3$H-SP added until a saturation point is reached. A Scatchard analysis of these data suggests that a single receptor is involved and that $^3$H-SP has a high affinity for this receptor. With regard to sensitivity, known SP agonists and antagonists inhibit $^3$H-SP binding. With regard to specificity, known substances structurally unrelated to SP including capsaicin and baclofen do not affect $^3$H-SP binding.

The results are expressed either as percent inhibition at a concentration of 30 micromoles per liter ($\mu$M) or as an IC50 calculated as the concentration in micromoles per liter. The compounds tested and found to be inhibitors in the submaxillary gland tissue preparation and then tested in the brain tissue preparation were found to have approximately the same degree of inhibition in both preparations.

Guinea Pig Ileum Test

Strips of longitudinal muscle derived from terminal ileum of adult male guinea pigs (Charles River, 400–600 g.) are mounted in 5-ml. organ baths containing oxygenated Krebs solution containing 1 $\mu$M each of atropine and pyrilamine maintained at 30–33 C. and connected to isometric transducers. Following tissue equilibration and repeated washing (45–60 min.), SP or an appropriate reference agonist is added cumulatively to the bath and contractions of the tissue are recorded. The bath is washed thoroughly and 30–45 min. is allowed to elapse before construction of a second reference agonist curve to assure reproducibility of the responses. Test compounds are similarly evaluated for agonist activity up to a maximum concentration of 10-100 μM. Regression analysis of the linear portion of the log concentration-percent maximal response curves provides the EC50 (and 95% confidence limits), the standard measure of agonist potency. When appropriate, relative molar potency ratios are calculated (EC50 reference/ED50 test drug). Antagonist activity is examined by pretreating thoroughly washed tissues with test compound (using a standard 5-10 min. contact time), then constructing a cumulative dose-response curve to the reference agonist. The effects of several concentrations of test antagonist, pooled across separate experiments, provide dose-ratio (EC50 shift) data for a standard Schild plot analysis, with computation of the pA2.

Rat Vas Deferens Test

Rat vasa deferentia are suspended in organ baths containing warmed, oxygenated Krebs solution and repetitively field-stimulated (0.1 Hz., 1 msec. duration, monophasic pulses) through platinum wire ring electrodes. Rapid, regular contractions of the muscle are recorded via transducers on a Grass polygraph. SP and related tachykinins added to the bath evoke a dose-dependent, stable potentiation of these electrically-induced contractions. For routine screening, a 10 μM concentration of SP is applied to all tissues to produce a 2-6 fold increase in electrically-stimulated twitch height. SP antagonist compounds (1-30 μM) produce an immediate, dose-related reversal of the response of the tissue to SP, which is quantified by determination of an IC50.

Test Results

The following table shows the results of testing the hexapeptide amides of Formulas I-VIII and Examples 1-42 in the foregoing tests. The $^3$H-SP binding test results were obtained using rat submaxillary gland tissue for Examples 1-34 and rat brain tissue for Examples 35-42.

| Example | $^3$H-SP Binding % Inhibition | $^3$H-SP Binding IC50(μM) | Guinea Pig Ileum % Agonism | Guinea Pig Ileum pA2 | Rat Vas Deferens IC50(μM) |
|---|---|---|---|---|---|
| 1 | 17 | | 0.7 | | |
| 2 | 25 | | 31 | | |
| 3 | 93 | | 27 | | |
| 4 | 17 | | 0.3 | | |
| 5 | 75 | | 5 | | |
| 6 | 8 | | 4 | | |
| 7 | 48 | | 0.7 | | |
| 8 | 49 | | 3 | | |
| 9 | 22 | | 0.0009 | 5.6 | |
| 10 | 65 | | 10 | | |
| 11 | 11 | | 40 | | |
| 12 | 69 | 26.8 | 0.0001 | 5.6 | 13 |
| 13 | 15 | | 6 | | |
| 14 | 10 | | 0.05 | | |
| 15 | 10 | | 0.004 | | |
| 16 | 13 | | 0.2 | | |
| 17 | | 9.7, 16.1 | <0.01 | 5.7 | 4.1 |
| 18 | 90 | | 33 | | |
| 19 | 42 | | 1 | | |
| 20 | 20 | | 0.01 | | |
| 21 | 26 | | 0.003 | | |
| 22 | 50 | | 0.1 | 5.0 | |
| 23 | 53 | | <0.001 | 5.4 | 20 |
| 24 | 30 | | | | 50 |
| 25 | 33 | | | 4.9 | 23 |
| 26 | 12 | | 0.4 | | |
| 27 | 81 | | | | |
| 28 | 33 | | | | >>40 |
| 29 | 64 | | | | >>40 |
| 30 | 40 | | 4.8 | | |
| 31 | 47 | | | | 30 |
| 32 | 40 | | | | |
| 33 | 15 | | | | |
| 34 | 20 | | 5.2 | | |
| 35 | 46 | 43.6 | | 6.3 | |
| 36 | 82 | 11.5 | | 6.3 | |
| 37 | 62 | | | | |
| 38 | 68 | | | | |
| 39 | 46 | | | | |
| 40 | 9 | | | | |
| 41 | 79 | 13.3 | | | |
| 42 | 81 | | | | |

Mouse Acetylcholine-induced Writhing Test

Male Swiss-Webster mice (18-24 g.) are divided into groups of 8-15 mice. A test compound in a vehicle or the vehicle alone is administered intrathecally in a volume of 5 μl by the method of Hylden and Wilcox (European Journal of Pharmacology, vol. 67, pp. 313-316, 1980) except that caudal cutaneous incision is not performed prior to injection. Five minutes after the injection a solution of acetylcholine (3.2 mg./kg., the approximate ED90) in 0.9% aqueous sodium chloride is administered intraperitoneally to each mouse. A mouse not exhibiting one or more writhes during the next two-minute observation period is considered protected by the test compound. For test compounds which produce a graded dose-response ED50 values with 95% confidence limits are determined by probit analysis of the data.

In this test the hexapeptide amide of Example 17 was administered in doses of 0.1-30 μg/mouse in a 5% aqueous dextrose vehicle. ED50 values of 2.4 (1.2-7.4) and 4.1 (2.5-6.8) μg/mouse were obtained.

The compounds of Formulas I-VIII can be prepared for use as Substance P agonists and/or antagonists and as analgesics and/or antihypertensives for oral or parenteral administration in liquid or solid dosage form as solutions, suspensions, emulsions, capsules or tablets with conventional pharmaceutical vehicles and adjuncts by conventional pharmaceutical techniques.

We claim:
1. The hexapeptide amide having the structural formula

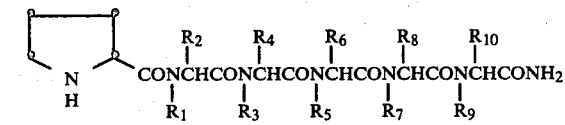

wherein
$R_1$, $R_5$, $R_7$ and $R_9$ taken alone are each independently hydrogen or methyl;
$R_2$ is phenyl, benzyl, p-chlorobenzyl, 4-pyridylmethyl or 3-indolylmethyl;
$R_3$ is hydrogen, methyl, benzyl or 2-phenylethyl;
$R_4$ is hydrogen, benzyl, p-chlorobenzyl, 2-phenylethyl or 4-pyridylmethyl;

R6 taken alone is hydrogen, methyl, benzyl, 4-pyridylmethyl, 3-indolylmethyl, aminomethyl, 4-aminobutyl, 3-guanidinopropyl or 2-carboxyethyl;

R6 taken together with R7 is ethylene;

R8 is 2-methylpropyl or dimethylaminomethyl; and

R10 is butyl or 2-methylthioethyl; and wherein each of the six amino acid moieties has the R or S configuration except the amino acid moiety bearing R2 when R2 is benzyl, which can only have the R configuration; or a pharmaceutically acceptable acid addition salt thereof.

2. A hexapeptide amide according to claim 1 selected from the group consisting of HPro-Phe-MePhe-Sar-Leu-MetNH2,
HPro-DPhe-Phe-DTrp-Leu-MetNH2,
HPro-DTrp-Phe-DTrp-Leu-MetNH2,
HPro-DPhe-LBpa-DTrp-Leu-MetNH2,
HPro-DPhe-DBpa-DTrp-Leu-MetNH2,
HPro-DPhe-Phe-DPhe-Leu-MetNH2,
HPro-LBpa-Phe-DPhe-Leu-MetNH2,
HPro-DBpa-Phe-DPhe-Leu-MetNH2,
HPro-DPhg-Phe-DPhe-Leu-MetNH2,
HPro-DPhe-Hfe-DPhe-Leu-MetNH2,
HPro-DPhe-Bgl-DPhe-Leu-MetNH2,
HPro-DPhe-Phe-DPhe-Leu-NleNH2,
HPro-DPhe-Pgl-DPhe-Leu-MetNH2
HPro-DTrp-Phe-DLys-Leu-MetNH2,
HPro-DTrp-Phe-DArg-Leu-MetNH2,
HPro-DTrp-Phe-DTrp-MeLeu-MetNH2,
HPro-DTrp-Phe-DTrp-Leu-MeMetNH2,
HPro-Pcp-Pcp-Gly-Leu-MetNH2,
HPro-DTrp-MePhe-DTrp-Leu-MetNH2,
HPro-DTrp-Gly-DTrp-Leu-MetNH2,
HPro-DTrp-Phe-MeDTrp-Leu-MetNH2,
HPro-DTrp-Phe-DTrp-Leu-NleNH2 and
HPro-MeDTrp-Phe-DTrp-Leu-MetNH2 or a pharmaceutically acceptable acid addition salt thereof.

3. A hexapeptide amide according to claim 1 wherein R2 is 3-indolylmethyl and R6 is 3-indolylmethyl or a pharmaceutically acceptable acid addition salt thereof.

4. The hexapeptide amide having the structural formula

HPro-X2-Phe-Gly-Leu-MetNH2 wherein X2 is DPhe or MePhe or a pharmaceutically acceptable acid addition salt thereof.

5. The hexapeptide amide having the structural formula

HPro-Phe-X3-Gly-Leu-MetNH2 wherein X3 is DPhe, MePhe, D,LBpa, DBpa or LBpa or a pharmaceutically acceptable acid addition salt thereof.

6. The hexapeptide amide having the structural formula

HPro-Phe-Phe-X4-Leu-MetNH2 wherein X4 is DAla, Sar, LDap, Glu, LBpa or DBpa or a pharmaceutically acceptable acid addition salt thereof.

7. The hexapeptide amide having the structural formula

HPro-Phe-Phe-Gly-X5-MetNH2 wherein X5 is DLeu, MeLeu or Gal or a pharmaceutically acceptable acid addition salt thereof.

8. The hexapeptide amide having the structural formula

HPro-Phe-Phe-Gly-Leu-X6-NH2 wherein X6 is DMet or Nle or a pharmaceutically acceptable acid addition salt thereof.

9. The hexapeptide amide having the structural formula

HDPro-Phe-Phe-Gly-Leu-MetNH2 or a pharmaceutically acceptable acid addition salt thereof.

10. The hexapeptide amide having the structural formula

HPro-Phe-Phe-CabLeu-MetNH2 or a pharmaceutically acceptable acid addition salt thereof.

* * * * *